(12) United States Patent
Van Willigengburg

(10) Patent No.: US 11,174,209 B2
(45) Date of Patent: Nov. 16, 2021

(54) C3 FRACTIONATION SYSTEM

(71) Applicant: SABIC Global Technologies, B.V., Bergen op Zoom (NL)

(72) Inventor: Joris Van Willigengburg, Maastricht (NL)

(73) Assignee: SABIC GLOBAL TECHNOLOGIES B.V., Bergen Op Zoom (NL)

(*) Notice: Subject to any disclaimer, the term of this patent is extended or adjusted under 35 U.S.C. 154(b) by 128 days.

(21) Appl. No.: 16/475,288

(22) PCT Filed: Jan. 2, 2018

(86) PCT No.: PCT/IB2018/050025
§ 371 (c)(1),
(2) Date: Jul. 1, 2019

(87) PCT Pub. No.: WO2018/122826
PCT Pub. Date: Jul. 5, 2018

(65) Prior Publication Data
US 2019/0330127 A1  Oct. 31, 2019

(30) Foreign Application Priority Data
Jan. 2, 2017 (EP) .................................. 17150023

(51) Int. Cl.
*C07C 7/09* (2006.01)
*B01J 19/24* (2006.01)
(Continued)

(52) U.S. Cl.
CPC ................... *C07C 7/09* (2013.01); *B01J 3/00* (2013.01); *B01J 19/18* (2013.01); *B01J 19/24* (2013.01);
(Continued)

(58) Field of Classification Search
CPC .... C07C 7/09; C07C 2/64; B01J 19/24; B01J 3/00; B01J 19/18; B01J 19/245;
(Continued)

(56) References Cited

U.S. PATENT DOCUMENTS 5,847,253 A * 12/1998 Ho ........................ C07C 15/02
585/450
8,128,895 B2 * 3/2012 Schultz ..................... C07C 2/66
422/608

(Continued)

OTHER PUBLICATIONS

China Office Action and Search Report for China Application No. 2018800057133; Application Filing Date: Jan. 2, 2018; Date of Search Jun. 28, 2021; with English Translation, 23 pages.

*Primary Examiner* — Youngsul Jeong
(74) *Attorney, Agent, or Firm* — Cantor Colburn LLP

(57) ABSTRACT

A C3 hydrocarbon fractionation system includes: a) a unit for providing a feed containing mainly propane and propylene, b) a C3 fractionation column for separating the feed to provide a top product richer in propylene than the feed and a bottom product leaner in propylene than the feed, wherein the bottom product comprises at least 50 wt % of propylene and c) a cumene production unit comprising an alkylation reactor for producing cumene from a propylene feed and a benzene feed, wherein the propylene feed comprises the bottom product of the C3 fractionation column.

20 Claims, 1 Drawing Sheet

(51) Int. Cl.
  *C07C 2/64* (2006.01)
  *F25J 3/06* (2006.01)
  *B01J 19/18* (2006.01)
  *B01J 3/00* (2006.01)
(52) U.S. Cl.
  CPC ......... *B01J 19/245* (2013.01); *B01J 19/2465* (2013.01); *C07C 2/64* (2013.01); *F25J 3/061* (2013.01); *F25J 3/0645* (2013.01); *B01J 2219/00* (2013.01)
(58) Field of Classification Search
  CPC ....... B01J 19/2465; B01J 2219/00; F25J 3/06; F25J 3/061; F25J 3/0645
  See application file for complete search history.

(56) References Cited

U.S. PATENT DOCUMENTS

| | | | |
|---|---|---|---|
| 8,563,793 B2 * | 10/2013 | Zimmermann | ......... C07C 5/333 585/302 |
| 10,450,241 B2 | 10/2019 | Panditrao et al. | |
| 2002/0016520 A1 * | 2/2002 | Paggini | ................ C07C 15/085 585/323 |
| 2005/0054888 A1 | 3/2005 | Hildreth et al. | |

* cited by examiner

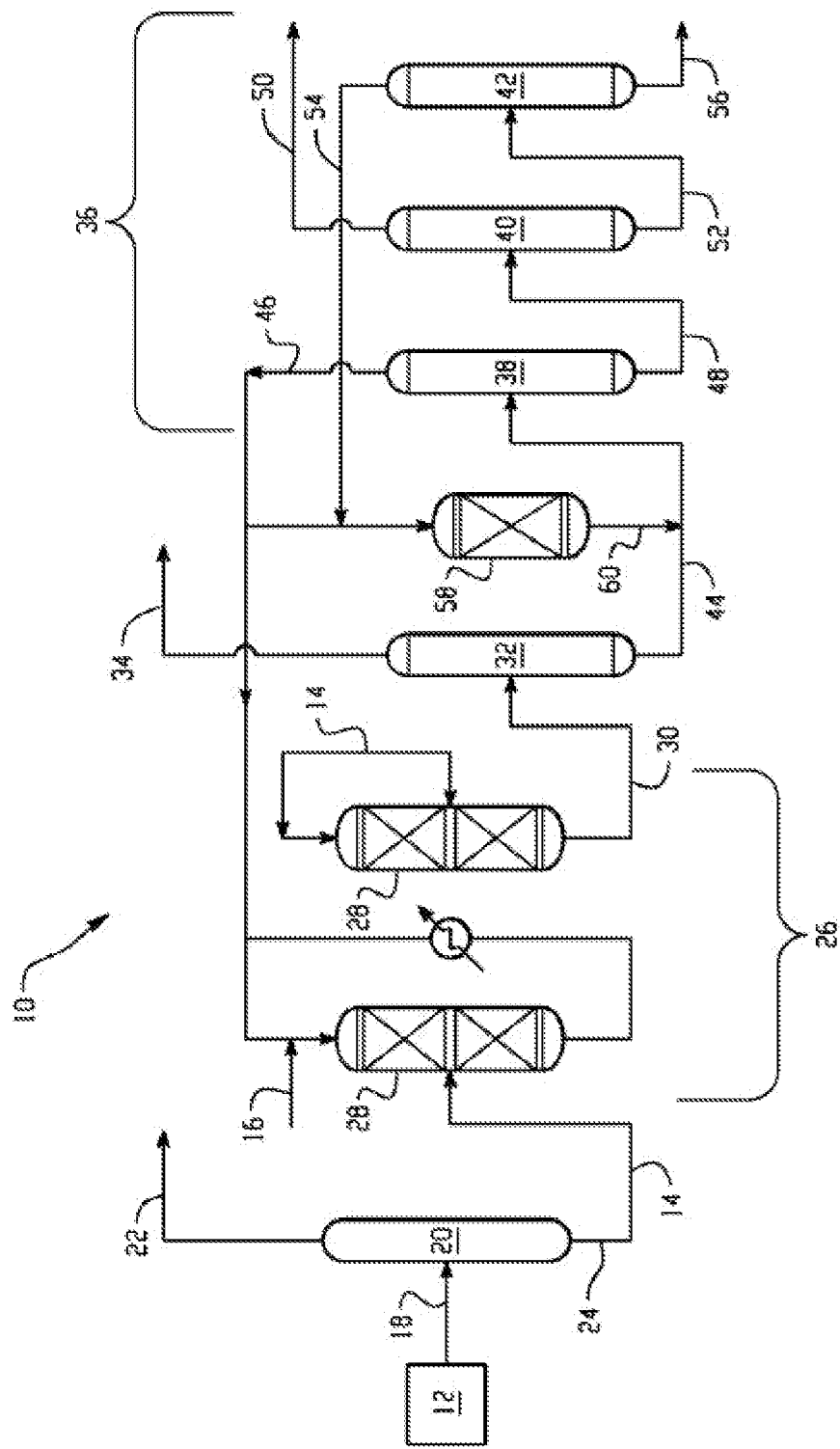

C3 FRACTIONATION SYSTEM

CROSS REFERENCE TO RELATED APPLICATIONS

This application is a National Stage application, i.e., a 371 of PCT/IB2018/050025, filed Jan. 2, 2018, which is incorporated herein by reference in its entirety, and which claims the benefit of European Application No. 17150023.4, filed Jan. 2, 2017.

TECHNICAL FIELD

The present application relates to a C3 fractionation system and a process using such system.

BACKGROUND

Propylene can be produced by propylene fractionation using a C3 splitter column in which propylene is separated from propane. Typically the feed is chemical grade propylene, which is the C3 fraction (typically 93-95 wt % min. propylene) produced by a steam cracker after hydrogenation or removal of the methyl-acetylene and propadiene. Polymer-grade propylene (>99.5 wt %) is produced as an overhead product. This separation to polymer grade propylene requires typically 150-230 stages and a reflux ratio of 20 because of the close boiling points of propylene and propane. A propane rich stream is produced as a bottom product.

Most of propylene ends up in the overhead, but some amount of propylene ends up in the bottom product mainly comprising propane. The bottom product is typically sold as a fuel or used as feedstock for the steam cracker. A high amount of the bottom product or a high concentration of propylene in the bottom product will result in a greater loss of propylene.

It is noted that US20020016520 discloses an integrated process for the preparation of cumene which comprises dehydrogenating a stream of propane to propylene in a dehydrogenation unit and sending the stream leaving the dehydrogenation unit, containing 25-40% by weight of propylene, to an alkylation unit together with a stream of benzene. US20020016520 does not disclose a C3 fractionation column. US20020016520 does not disclose fractionating a stream to a propylene-rich product and a propylene-lean product and using the propylene-lean product for cumene production.

It is an objective of the present application to provide a system which allows more efficient use of the materials used and produced.

SUMMARY

Disclosed, in various embodiments, are systems and processes for C3 fractionation.

Accordingly, disclosed herein is a C3 fractionation system that includes: a) a unit for providing a feed containing mainly propane and propylene, b) a C3 fractionation column for separating the feed to provide a top product richer in propylene than the feed and a bottom product leaner in propylene than the feed, wherein the bottom product comprises at least 50 wt % of propylene and c) a cumene production unit comprising an alkylation reactor for producing cumene from a propylene feed and a benzene feed, wherein the propylene feed comprises the bottom product of the C3 fractionation column.

Also disclosed herein is a process for C3 hydrocarbon fraction that includes: feeding propane and propylene to a unit; separating the feed in a C3 fractionation column to provide a top product richer in propylene than the feed and a bottom product leaner in propylene than the feed, wherein the bottom product comprises at least 50 weight % of propylene; and producing cumene in a cumene production unit comprising an alkylation reactor from a propylene feed and a benzene feed, wherein the propylene feed comprises the bottom product of the C3 fractionation column.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

The FIGURE is a schematic diagram of the system disclosed herein.

DETAILED DESCRIPTION

The term "C3" is herein understood as hydrocarbons having 3 carbon atoms. In known C3 fractionation columns, the separation is performed with the objective of obtaining a bottom product wherein the concentration of propylene is as low as possible. In the system presently disclosed system, the fractionation is performed by producing a relatively large amount of the propylene-lean bottom product which leads to the bottom product comprising a relatively high amount of propylene. This bottom product is then used by a cumene production unit to produce cumene. By separating the feed in such a manner (increased bottom product), more feed can be processed while producing the top product of the same purity using the same C3 fractionation column. Without changing the C3 fractionation column, the system presently disclosed can also allow obtaining a higher purity top product from the same feed, or using a feed with a lower concentration of propylene to obtain the top product with the same purity.

The bottom product contains sufficiently high concentration of propylene to be used by a cumene production unit. The cumene production unit produces cumene and a propane rich product. The propane rich product can be separated off and can be used as a fuel or used as feedstock for the steam cracker, in the same way as the bottom feed from a conventional C3 fractionation column.

Unit a)

The system comprises a) a unit for providing a feed containing mainly propane and propylene. The unit can, e.g., comprise a propane dehydrogenation unit, a steam cracker or a fluid catalytic cracker. These are per se well-known and are not herein described further in detail. The unit for providing the feed may be one unit or a combination of different types of units. In some preferred embodiments, the unit a) comprises a propane dehydrogenation unit and a steam cracker. The propane dehydrogenation unit, steam cracker or the fluid catalytic cracker may be followed by a unit for removing components other than propane and propylene for providing the feed with a desired concentration of propane and propylene.

Preferably, the total amount of propane and propylene in the feed is at least 95 volume % (vol %), more preferably at least 97 vol %, more preferably at least 99 vol %, more preferably at least 99.5 vol %. Typically, the remaining components in the feed are C2 hydrocarbons such as ethane or unreacted hydrogen from an upstream methyl-acetylene and propadiene hydrogenation reactor.

Preferably, the amount of propylene in the feed is at least 85 vol %, more preferably at least 90 vol %, more preferably at least 95 vol %.

The amount of propane in the feed can be, for example, 1-15 vol % or 3-10 vol %.

Unit b)

The system comprises a C3 fractionation column for separating the feed to a propylene-rich top product and a propylene-lean bottom product.

Preferably, the amount of propylene in the top product is at least 98 vol %, more preferably at least 99 vol %, more preferably at least 99.5 vol %.

Preferably, the amount of propane in the top product is at most 2 vol %, more preferably at most 1 vol %, more preferably at most 0.5 vol %.

Preferably, the amount of propylene in the bottom product is 50-95 vol %, for example 60-90 vol % or 70-80 vol %.

Preferably, the amount of propane in the bottom product is 1-20 vol %, for example 3-15 vol % or 5-10 vol %.

Unit c)

The system comprises a cumene production unit comprising an alkylation reactor for producing cumene from a propylene feed and a benzene feed, wherein the propylene feed comprises the bottom product of the C3 fractionation column. The benzene feed can be from any suitable unit.

Using a propylene feedstream having a wide range of purity for cumene production is known from Polimeri Europa and Lummus Technology. PBE-1 zeolite based catalyst process can be fed with propylene at a very wide range of purity, from de-hydro and refinery to chemical and polymer grade, with a propane content from 50 to 1% by weight, as mentioned in a document "Cumene with proprietary catalyst PBE-1 zeolite based Proprietary process technology" retrieved from https://www.eni.com/it_IT/attachments/azienda/attivita-strategie/petrolchimica/licensing/Cumene-A4-lug09.pdf.

Cumene is made by the alkylation of benzene with propylene, which produces a product stream comprising C3 hydrocarbons, benzene, cumene and poly-isopropylbenzene.

The C3 hydrocarbons in the product stream are rich in propane since propylene has reacted with benzene. Preferably, the cumene production unit further comprises a separation unit for separating the C3 hydrocarbons from the product stream to produce a C3 lean product stream. Preferably, the C3 hydrocarbons are recycled back to the unit a). In case the unit a) is a propane dehydrogenation unit, the ultimate yield of propylene is thereby increased. In case the unit a) is a steam cracker, the ultimate yield of ethylene and propylene is increased. The cumene production unit further comprises a distillation train following the separation unit for separating the C3 hydrocarbons from the product stream.

The distillation train comprises a benzene column, a cumene column and a poly-isopropylbenzene column. The C3 lean product stream is fed to the benzene column to produce a top product comprising benzene and a bottom product. The bottom product from the benzene column is fed to the cumene column to produce a top product comprising cumene and a bottom product. The bottom product from the cumene column is fed to the poly-isopropylbenzene column to produce a top product comprising poly-isopropylbenzene. The poly-isopropylbenzene column may produce a bottom product comprises high boilers which can be used as fuel.

Preferably, at least part of the top product from the benzene column is recycled back to the alkylation reactor.

Preferably, the cumene production unit further comprises a transalkylation reactor for being fed with the top product from the poly-isopropylbenzene column. The transalkylation of the poly-isopropylbenzene from the poly-isopropylbenzene column produces additional cumene for increasing the cumene yield. The product from the transalkylation reactor is fed to the benzene column.

The presently disclosed system further relates to a process for C3 fractionation using the system according to the presently disclosed system and process. The process can include providing the feed containing mainly propane and propylene, separating the feed to provide the top product and the bottom product and producing cumene from the propylene feed and the benzene feed.

A more complete understanding of the components, processes, and apparatuses disclosed herein can be obtained by reference to the accompanying drawings. These FIGURES (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The FIGURE shows a C3 hydrocarbon fractionation system 10 as described herein where a) a unit 12 for providing a feed 18 comprising propane and propylene is provided along with b) a C3 fractionation column 20 for separating the feed 18 to provide a top product 22 richer in propylene than the feed and a bottom product 24 leaner in propylene than the feed, wherein the bottom product 24 comprises at least 50 weight % of propylene; and c) a cumene production unit 26 comprising an alkylation reactor 28 for producing cumene from a propylene feed 14 and a benzene feed 16, wherein the propylene feed 14 comprises the bottom product of the C3 fractionation column 20.

The alkylation reactor 28 produces a product stream 30 comprising C3 hydrocarbons, benzene, cumene and poly-isopropylbenzene, wherein the cumene production unit 26 further comprises a separation unit 32 for separating the C3 hydrocarbons from the product stream to produce a C3 lean product stream 44. A C3 hydrocarbon stream 34 from the separation unit 32 is recycled back to the unit a) 12.

The cumene production unit 26 further comprises a distillation train 36 following the separation unit 32, comprising a benzene column 38, a cumene column 40 and a poly-isopropylbenzene column 42. The C3 lean product stream 44 is fed to the benzene column 38 to produce a top product 46 comprising benzene and a bottom product, the bottom product 48 from the benzene column 38 is fed to the cumene column 40 to produce a top product 50 comprising cumene and a bottom product 52 and the bottom product 52 from the cumene column 40 is fed to the poly-isopropylbenzene column 42 to produce a top product 54 comprising poly-isopropylbenzene and a bottom product 56 comprising heavies. At least part of the top product 46 from the benzene column 38 is recycled back to the alkylation reactor 28.

The cumene production unit 26 further comprises a transalkylation reactor 58 for being fed with the top product 54 from the poly-isopropylbenzene column 42 and at least part of the top product 46 from the benzene column 38, for producing a transalkylated product stream 60 to be fed to the benzene column 38.

The systems and processes disclosed herein include at least the following aspects:

Aspect 1: A C3 hydrocarbon fractionation system, comprising: a) a unit for providing a feed comprising propane and propylene; b) a C3 fractionation column for separating the feed to provide a top product richer in propylene than the feed and a bottom product leaner in propylene than the feed, wherein the bottom product comprises at least 50 weight % of propylene; and c) a cumene production unit comprising an alkylation reactor for producing cumene from a propylene feed and a benzene feed, wherein the propylene feed comprises the bottom product of the C3 fractionation column.

Aspect 2: The system according to Aspect 1, wherein the unit a) comprises one or more of the group consisting of a propane dehydrogenation unit, a steam cracker or a fluid catalytic cracker.

Aspect 3: The system according to any one of the preceding aspects, wherein the unit a) comprises a propane dehydrogenation unit and a steam cracker.

Aspect 4: The system according to any one of the preceding aspects, wherein the total amount of propane and propylene in the feed is at least 95 vol %, preferably at least 97 vol %, more preferably at least 99 vol %, more preferably at least 99.5 vol %.

Aspect 5: The system according to any one of the preceding aspects, wherein the amount of propylene in the feed is at least 85 vol %, preferably at least 90 vol %, more preferably at least 95 vol %.

Aspect 6: The system according to any one of the preceding aspects, wherein the amount of propylene in the top product is at least 98 vol % %, more preferably at least 99 vol %, more preferably at least 99.5 vol %.

Aspect 7: The system according to any one of the preceding aspects, the amount of propylene in the bottom product is 50-95 vol %, for example 60-90 vol % or 70-80 vol %.

Aspect 8: The system according to any one of the preceding aspects, wherein the alkylation reactor produces a product stream comprising a product stream comprising C3 hydrocarbons, benzene, cumene and poly-isopropylbenzene, wherein the cumene production unit further comprises a separation unit for separating the C3 hydrocarbons from the product stream to produce a C3 lean product stream.

Aspect 9: The system according to Aspect 8, wherein the C3 hydrocarbons from the separation unit are recycled back to the unit a).

Aspect 10: The system according to Aspect 8 or 9, wherein the cumene production unit further comprises a distillation train following the separation unit, comprising a benzene column, a cumene column and a poly-isopropylbenzene column, wherein the C3 lean product stream is fed to the benzene column to produce a top product comprising benzene and a bottom product, the bottom product from the benzene column is fed to the cumene column to produce a top product comprising cumene and a bottom product and the bottom product from the cumene column is fed to the poly-isopropylbenzene column to produce a top product comprising poly-isopropylbenzene.

Aspect 11: The system according to Aspect 10, wherein at least part of the top product from the benzene column is recycled back to the alkylation reactor.

Aspect 12: The system according to Aspect 10 or 11, wherein the cumene production unit further comprises a transalkylation reactor for being fed with the top product from the poly-isopropylbenzene column and at least part of the top product from the benzene column, for producing a transalkylated product stream to be fed to the benzene column.

Aspect 13: A process for C3 hydrocarbon fractionation using the system according to any one of the preceding aspects, comprising the steps of: providing the feed containing mainly propane and propylene, separating the feed to provide the top product and the bottom product and producing cumene from the propylene feed and the benzene feed.

Aspect 14: A process for C3 hydrocarbon fraction comprising: feeding propane and propylene to a unit; separating the feed in a C3 fractionation column to provide a top product richer in propylene than the feed and a bottom product leaner in propylene than the feed, wherein the bottom product comprises at least 50 weight % of propylene; and producing cumene in a cumene production unit comprising an alkylation reactor from a propylene feed and a benzene feed, wherein the propylene feed comprises the bottom product of the C3 fractionation column.

Aspect 15: The process according to Aspect 14, further comprising producing a product stream from the alkylation reactor comprising C3 hydrocarbons, benzene, cumene and poly-isopropylbenzene, and producing a C3 lean product stream from a separation unit in the cumene production unit.

Aspect 16: The process according to Aspect 15, further comprising recycling the C3 hydrocarbons from the separation unit to the unit.

Aspect 17: The process according to any of Aspects 14-16, wherein the cumene production unit further comprises a distillation train following the separation unit, comprising a benzene column, a cumene column and a poly-isopropylbenzene column, wherein the C3 lean product stream is fed to the benzene column to produce a top product comprising benzene and a bottom product, the bottom product from the benzene column is fed to the cumene column to produce a top product comprising cumene and a bottom product and the bottom product from the cumene column is fed to the poly-isopropylbenzene column to produce a top product comprising poly-isopropylbenzene.

Aspect 18: The process according to Aspect 17, further comprising recycling at least part of the top product from the benzene column to the alkylation reactor.

Aspect 19: The process according to any of Aspects 17 or 18, wherein the cumene production unit further comprises a transalkylation reactor for being fed with the top product from the poly-isopropylbenzene column and at least part of the top product from the benzene column, for producing a transalkylated product stream to be fed to the benzene column.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

When values are mentioned for a lower limit and an upper limit for a parameter, ranges made by the combinations of the values of the lower limit and the values of the upper limit are also understood to be disclosed.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "+10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A C3 hydrocarbon fractionation system, comprising:
   a) a unit for providing a feed comprising propane and propylene;
   b) a C3 fractionation column for separating the feed to provide a top product richer in propylene than the feed and a bottom product leaner in propylene than the feed, wherein the bottom product comprises at least 50 weight % of propylene, based on a total weight of the bottom product, and an amount of propylene in the top product is at least 98 vol %, based on a total volume of the top product; and
   c) a cumene production unit comprising
      an alkylation reactor for producing a product stream comprising cumene from a propylene feed and a benzene feed, wherein the propylene feed comprises the bottom product of the C3 fractionation column,
      a distillation train comprising a benzene column, a cumene column, and a poly-isopropylbenzene column, wherein
         a product stream from the alkylation reactor is fed to the benzene column to produce a top product comprising benzene and a bottom product,
         the bottom product from the benzene column is fed to the cumene column to produce a top product comprising cumene and a bottom product, and
         the bottom product from the cumene column is fed to the poly-isopropylbenzene column to produce a top product comprising poly-isopropylbenzene, and
      a transalkylation reactor to be fed with the top product from the poly-isopropylbenzene column and at least part of the top product from the benzene column, for producing a transalkylated product stream to be fed to the benzene column.

2. The system according to claim 1, wherein the unit a) comprises one or more of the group consisting of a propane dehydrogenation unit, a steam cracker, and a fluid catalytic cracker.

3. The system according to claim 1, wherein the unit a) comprises a propane dehydrogenation unit and a steam cracker.

4. The system according to claim 1, wherein a total amount of propane and propylene in the feed is at least 95 vol %, based on a total volume of the feed.

5. The system according to claim 1, wherein an amount of propylene in the feed is at least 85 vol %, based on a total volume of the feed.

6. The system according to claim 1, wherein an amount of propylene in the top product of the C3 fractionation column is at least 99 vol %, based on a total volume of the top product of the C3 fractionation column.

7. The system according to claim 1, wherein an amount of propylene in the bottom product of the C3 fractionation column is 60-90 vol %, based on a total volume of the bottom product of the C3 fractionation column.

8. The system according to claim 1, wherein the alkylation reactor produces the product stream comprising C3 hydrocarbons, benzene, cumene, and poly-isopropylbenzene, and wherein the cumene production unit further comprises a separation unit for separating the C3 hydrocarbons from the product stream of the alkylation reactor to produce a C3 lean product stream.

9. The system according to claim 8, wherein the C3 hydrocarbons from the separation unit are recycled back to the unit a).

10. The system according to claim 1, wherein an amount of propylene in the bottom product of the C3 fractionation column is 70-80 vol %, based on a total volume of the bottom product of the C3 fractionation column, and an amount of propylene in the top product of the C3 fractionation column is at least 99.5 vol %, based on a total volume of the top product of the C3 fractionation column.

11. A C3 hydrocarbon fractionation system, comprising:
a) a unit for providing a feed comprising propane and propylene;
b) a C3 fractionation column for separating the feed to provide a top product richer in propylene than the feed and a bottom product leaner in propylene than the feed, wherein the bottom product comprises at least 50 weight % of propylene, based on a total weight of the bottom product; and
c) a cumene production unit comprising an alkylation reactor for producing cumene from a propylene feed and a benzene feed, wherein the propylene feed comprises the bottom product of the C3 fractionation column,
wherein the alkylation reactor produces a product stream comprising C3 hydrocarbons, benzene, cumene, and poly-isopropylbenzene, and wherein the cumene production unit further comprises a separation unit for separating the C3 hydrocarbons from the product stream to produce a C3 lean product stream,
the cumene production unit further comprises a distillation train following the separation unit, the distillation train comprising a benzene column, a cumene column, and a poly-isopropylbenzene column, wherein
the C3 lean product stream is fed to the benzene column to produce a top product comprising benzene and a bottom product,
the bottom product from the benzene column is fed to the cumene column to produce a top product comprising cumene and a bottom product, and
the bottom product from the cumene column is fed to the poly-isopropylbenzene column to produce a top product comprising poly-isopropylbenzene.

12. The system according to claim 11, wherein at least part of the top product from the benzene column is recycled back to the alkylation reactor.

13. The system according to claim 11, wherein the cumene production unit further comprises a transalkylation reactor to be fed with the top product from the poly-isopropylbenzene column and at least part of the top product from the benzene column, for producing a transalkylated product stream to be fed to the benzene column.

14. A process for C3 hydrocarbon fractionation using the system according to claim 1, comprising the steps of: providing the feed comprising propane and propylene, separating the feed to provide the top product and the bottom product, and producing the cumene from the propylene feed and the benzene feed.

15. The process according to claim 14, further comprising producing a product stream from the alkylation reactor comprising C3 hydrocarbons, benzene, cumene, and poly-isopropylbenzene, and producing a C3 lean product stream from a separation unit in the cumene production unit by separating the C3 hydrocarbons from the product stream in the separation unit.

16. The process according to claim 15, further comprising recycling the C3 hydrocarbons from the separation unit to the unit providing the feed comprising the propane and the propylene.

17. The process according to claim 15, wherein the cumene production unit further comprises a distillation train following the separation unit, the distillation train comprising a benzene column, a cumene column, and a poly-isopropylbenzene column, and wherein the process further comprises
feeding the C3 lean product stream to the benzene column to produce a top product comprising benzene and a bottom product,
feeding the bottom product from the benzene column to the cumene column to produce a top product comprising cumene and a bottom product, and
feeding the bottom product from the cumene column to the poly-isopropylbenzene column to produce a top product comprising poly-isopropylbenzene.

18. The process according to claim 17, further comprising recycling at least part of the top product from the benzene column to the alkylation reactor.

19. The process according to claim 17, wherein the cumene production unit further comprises a transalkylation reactor to be fed with the top product from the poly-isopropylbenzene column and at least part of the top product from the benzene column, for producing a transalkylated product stream to be fed to the benzene column.

20. A process for C3 hydrocarbon fractionation comprising:
feeding propane and propylene to a unit to provide a feed comprising the propane and the propylene;
separating the feed in a C3 fractionation column to provide a top product richer in propylene than the feed and a bottom product leaner in propylene than the feed, wherein the bottom product comprises at least 50 weight % of propylene, based on a total weight of the bottom product;
producing cumene in a cumene production unit comprising an alkylation reactor from a propylene feed and a benzene feed, wherein the propylene feed comprises the bottom product of the C3 fractionation column;
producing a product stream from the alkylation reactor comprising C3 hydrocarbons, benzene, cumene, and poly-isopropylbenzene, and producing a C3 lean product stream from a separation unit in the cumene production unit by separating the C3 hydrocarbons from the product stream in the separation unit;
feeding the C3 lean product stream to a benzene column to produce a top product comprising benzene and a bottom product;
feeding the bottom product from the benzene column to a cumene column to produce a top product comprising cumene and a bottom product; and
feeding the bottom product from the cumene column to a poly-isopropylbenzene column to produce a top product comprising poly-isopropylbenzene.

* * * * *